US009295411B2

(12) United States Patent
Galasso

(10) Patent No.: US 9,295,411 B2
(45) Date of Patent: Mar. 29, 2016

(54) EXPANDABLE PLATFORM FOR MEASURING PLANTAR PRESSURES

(75) Inventor: Piero Galasso, Rome (IT)

(73) Assignee: Adriana Pengo, Rome (IT)

( * ) Notice: Subject to any disclaimer, the term of this patent is extended or adjusted under 35 U.S.C. 154(b) by 135 days.

(21) Appl. No.: 13/699,414

(22) PCT Filed: May 20, 2011

(86) PCT No.: PCT/IT2011/000168
§ 371 (c)(1),
(2), (4) Date: Nov. 21, 2012

(87) PCT Pub. No.: WO2011/145130
PCT Pub. Date: Nov. 24, 2011

(65) Prior Publication Data
US 2013/0072819 A1   Mar. 21, 2013

(30) Foreign Application Priority Data

May 21, 2010   (IT) .............................. RM2010A0266

(51) Int. Cl.
*A61B 5/103*   (2006.01)

(52) U.S. Cl.
CPC .................................... *A61B 5/1036* (2013.01)

(58) Field of Classification Search
CPC ............................ A61B 5/1036; A61B 5/1038
USPC ........................................................ 600/592
See application file for complete search history.

(56) References Cited

U.S. PATENT DOCUMENTS

| 4,843,891 | A | 7/1989 | Brunner et al. |
| 5,945,610 | A | 8/1999 | Galasso |
| 6,505,522 | B1 | 1/2003 | Wilssens |
| 7,867,049 | B1 * | 1/2011 | Doffay ............................. 441/40 |
| 2007/0192045 | A1 * | 8/2007 | Brett et al. ....................... 702/42 |
| 2008/0191864 | A1 * | 8/2008 | Wolfson .................. G06F 3/011 340/524 |
| 2009/0051559 | A1 | 2/2009 | Wu et al. |
| 2015/0374264 | A1 * | 12/2015 | Haas ...................... A61B 5/112 73/862.541 |
| 2015/0374297 | A1 * | 12/2015 | Haas .................... A61B 5/6887 73/862.541 |

FOREIGN PATENT DOCUMENTS

| GB | 2 422 018 A | 7/2006 |
| WO | 02/17776 A2 | 3/2002 |

OTHER PUBLICATIONS

International Search Report, dated Aug. 9, 2011, from corresponding PCT application.

* cited by examiner

*Primary Examiner* — Adam J Eiseman
*Assistant Examiner* — Yasmeen S Warsi
(74) *Attorney, Agent, or Firm* — Young & Thompson

(57) ABSTRACT

An expandable platform for measuring plantar pressures includes a multiplicity of modules (1) for measuring plantar pressures, each having mutually orthogonal sides and including its own array of sensors able to measure plantar pressure, and a control computer provided with a software for the treatment of the information coming from the sensors, able to display the static, postural and dynamic examination of the plantar pressures. The array of plantar sensors of each module (1) is connected with the control computer through an interface (2) positioned inferiorly to the measuring module (1) in such a way that each measuring module (1) is individually connectable for the transmission of data with the control computer, and is electronically and mechanically joined to other measuring modules (1) positioned adjacent to its own mutually orthogonal sides.

10 Claims, 2 Drawing Sheets

EXPANDABLE PLATFORM FOR MEASURING PLANTAR PRESSURES

TECHNICAL FIELD

This invention relates to an expandable platform for measuring plantar pressures.

BACKGROUND ART

The pressures of the plantar support on the ground are currently acquired using baropodometric platforms equipped with resistive measurement sensors. The baropodometric platforms are used for measuring the support of the foot when still, static examination, and when moving, dynamic examination.

A baropodometric platform consists of a printed circuit in which the measurement sensors, connected to an interface which sends the data to a computer, are printed.

The current dimensions of the printed circuits currently produced do not allow baropodometric platforms to be made which are suitable for the measuring needs, that is, with dimensions and surface areas that allow the actual conditions of a still and moving foot to be measured.

In addition, the more the size of the circuit increases the more the number of sensors which may be used reduces, to the detriment of the requested resolution, a limit determined by the fact that the pressure information measured on a large surface area, to be then transmitted to the computer, would be excessive compared with the subsequent processing performed by the processor itself.

A further limitation of the systems currently proposed on the market is due to the type of construction of the current measuring modules, which requires that the components that operate the sensor electronics are mounted on one of the sides of the circuit.

DISCLOSURE OF THE INVENTION

The aim of this invention is to overcome the shortcomings of the prior art.

In particular, an aim of this invention is to provide an expandable platform which is extendable in all directions to cover any surface designed for the acquisition of plantar pressures.

Another aim of this invention is to provide an expandable platform in which the high speed transmission of data through the interface does not slow down the processing of the computer.

A further aim of this invention is to provide an expandable platform with a module which may be easily calibrated using signal sorting satellites that subdivide the module into specific areas, the areas being under the electronic control of the signals, that are electronically adjustable by software.

Yet another aim of this invention is to provide an expandable platform which, from the mechanical point of view, allows the modules to be easily connected together, creating an uninterrupted surface.

The technical purpose and aims specified are substantially achieved by an expandable platform for measuring plantar pressures comprising the technical features set out in one or more of the accompanying claims.

BRIEF DESCRIPTION OF THE DRAWINGS

Further features and advantages of this invention are more apparent from the non-limiting description which follows of a preferred, non-limiting embodiment of an expandable platform for measuring plantar pressures as illustrated in the accompanying drawings, in which.

DETAILED DESCRIPTION OF THE PREFERRED EMBODIMENTS OF THE INVENTION

Figure 1:
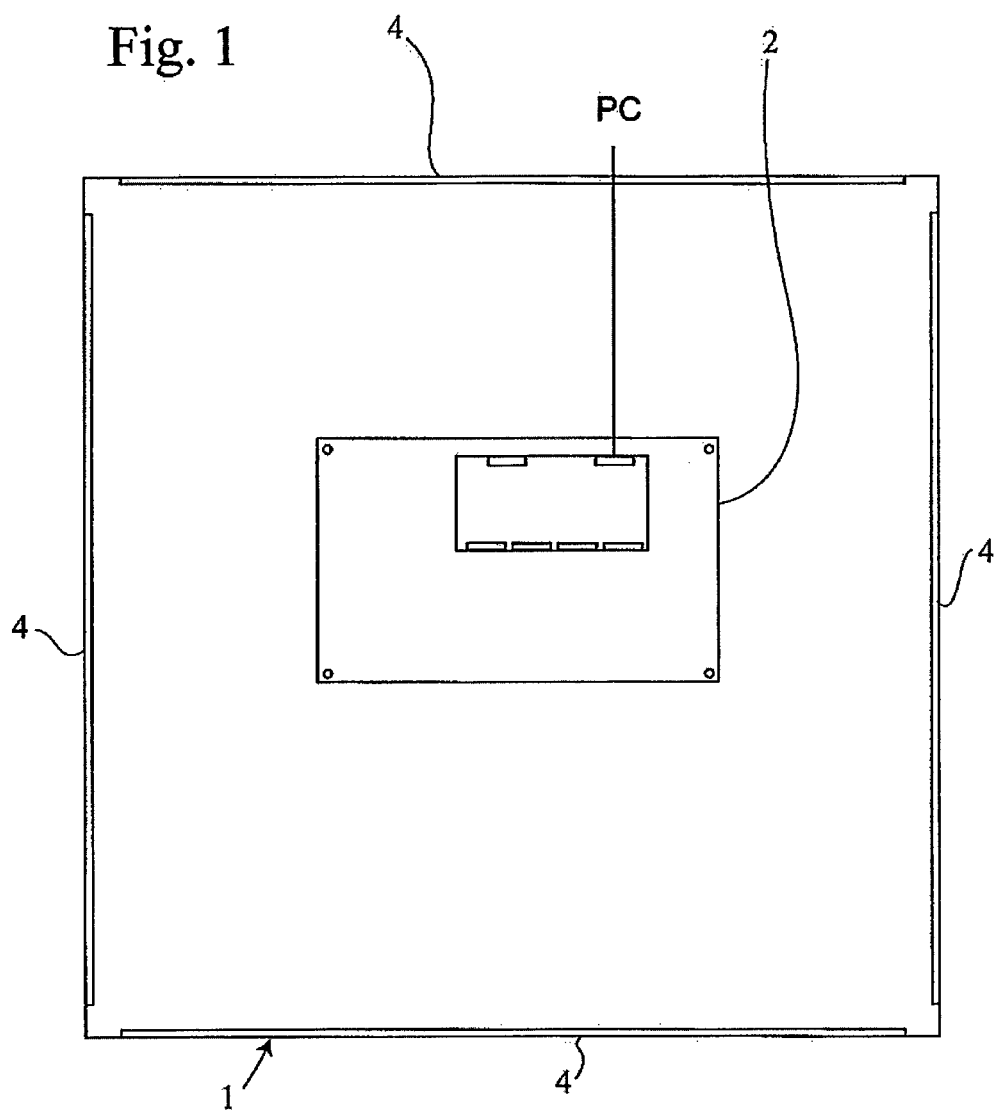
FIG. 1 is a schematic plan view from below of a module for measuring plantar pressures for the expandable platform according to this invention.

FIG. 1 shows a plan view from below of a module 1 for measuring plantar pressures used to make an expandable platform according to this invention, The module 1 has mutually orthogonal sides, having a square shape. It includes its own array of measuring sensors, distributed uniformly on all the modules beneath the foot supporting surface. The measuring sensors, which are not shown in detail because, like the structure of the module, they are of known type, are designed to measure the plantar pressure and transmit it to a control computer, which, in FIG. 1, is denoted with PC.

The control computer PC is equipped with software for the treatment of the information coming from the sensors and it is able to display the static, postural and dynamic examination of the plantar pressures.

According to the invention, the array of plantar sensors of each measuring module is connected with the control computer through an interface 2 positioned inferiorly to the module. In this way each measuring module 1 is individually connectable for the transmission of data with the control computer PC.

Figure 2:
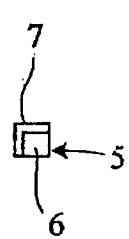

In addition, each module is electronically and mechanically joined to other measuring modules positioned adjacent to its own mutually orthogonal sides, as shown in FIG. 2, which is a schematic plan view from below of a measuring platform 3 according to this invention obtained with a plurality of plantar pressure measuring modules shown in FIG. 6. The measuring modules 1 positioned adjacent to their own mutually orthogonal sides are joined to each other by snap fittings shown in the plan views from above in FIGS. 2 to 5.

Each measuring module 1 is provided with a wall 4 on each side, which keeps the module 1 raised above the ground. The wall 4 is missing close to the corners of the measuring module 1 at which the modules are joined together by connecting means.

Figure 5:
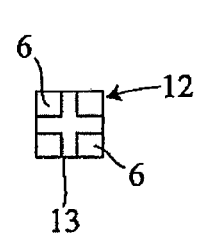
FIGS. 2 to 5 are plan views from above of snap fittings for several modules of FIG. 1.
Figure 4:
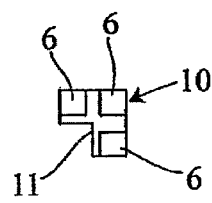
Figure 3:
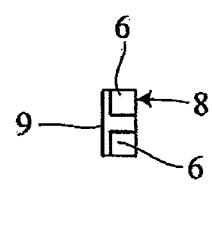

In particular, FIG. 2 shows connecting means 5 which, having an upper base 6 and angular wall portions 7 acts as simple infill when the module 1 does not have another adjacent module 1. FIG. 3 shows connecting means 8, with two bases 6 and T-shaped wall portions 9, designed to join externally two modules 1. FIG. 4 shows connecting means 10, with three bases 6 and cross-shaped wall portions 11, designed to join externally three modules 1. Lastly, FIG. 5 shows connecting means 12, with four bases 6 and cross-shaped wall portions 13, designed to join externally four modules 1.

Figure 6:
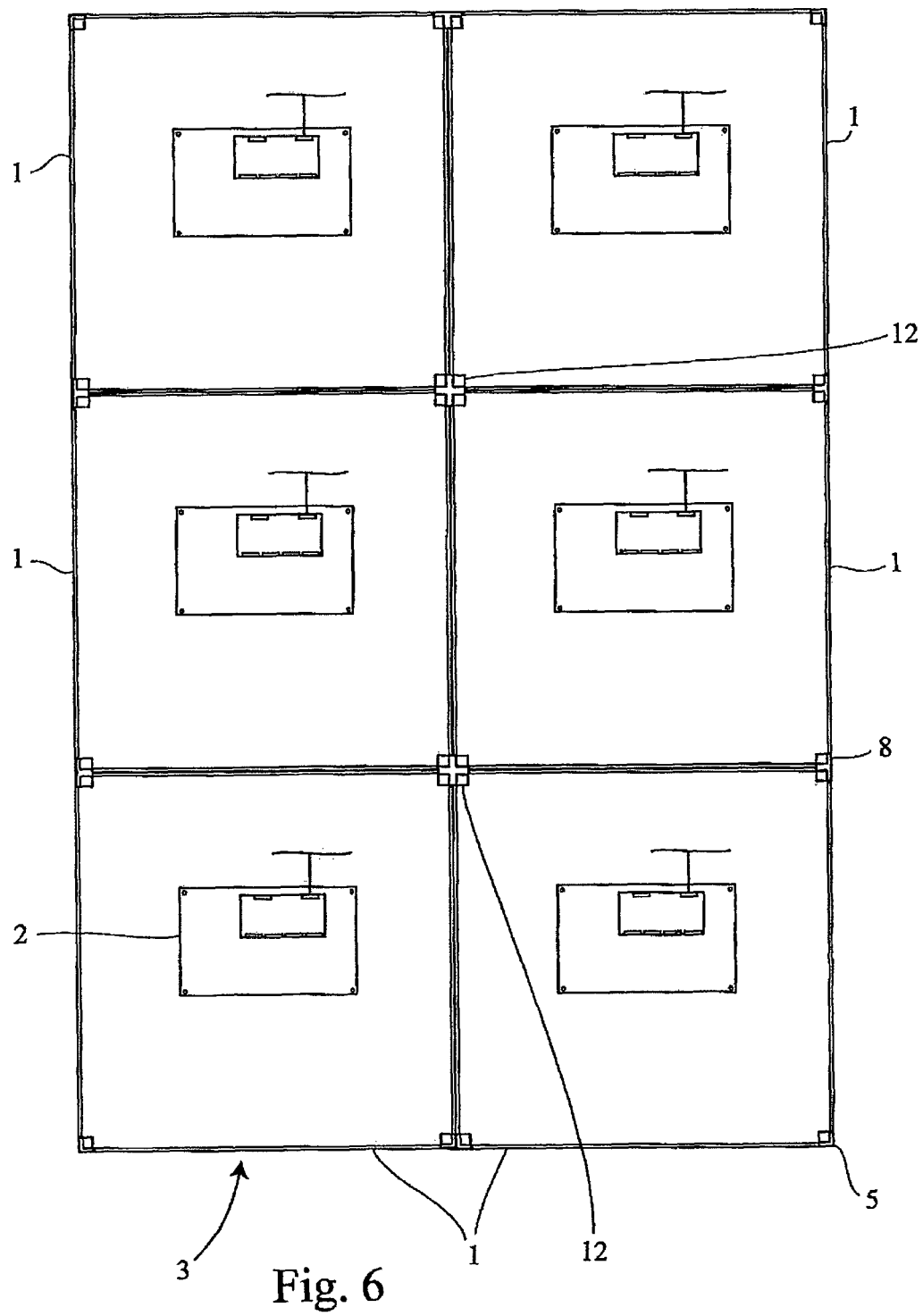
FIG. 6 is a schematic plan view from below of a measuring platform according to this invention obtained with a plurality of plantar pressure measuring modules shown in FIG. 1.

The joints between the modules 1 are clearly shown in FIG. 6.

It may be understood that there are no limits to the extension of the expandable platform according to this invention. It allows an entire room, a gym or a sports track to be covered, allowing the plantar pressures of one or more persons to be measured in any of their activities. It is possible to study the positions of the plantar support of a person walking in a room or of an athlete who performs an athletic movement, such as running, dancing or fencing.

The possibility of joining together several measuring modules without limits of extension in either length or width allows moving support surfaces to be scanned with precise sampling thanks to the high resolution and the speed of data transmission which does not require the computer to be interrupted during measurement.

The means of mechanical connection between the modules easily allows both the connection and fastening together of the modules, without creating dividing walls or interruption spaces between one module and another, and the passage of connection cables.

The invention claimed is:

1. An expandable platform for measuring plantar pressures, the platform comprising:
   a multiplicity of measuring modules (1), each said measuring module for measuring plural plantar pressures, each said measuring module including
   i) four mutually orthogonal sides,
   ii) four walls, each wall of said four walls extending along at least part of a respective one of said four mutually orthogonal sides,
   iii) an array of sensors that measure the plural plantar pressures, and
   iv) an interface and a control computer, both the interface and control computer positioned inferiorly to said four walls of said each measuring module (1),
   wherein the interface of said each measuring module is electronically connected to the respective array of sensors and is electronically connected to the respective control computer,
   wherein each control computer is provided with software for treatment of information transmitted from the sensors of each of the respective said measuring modules through the respective interface,
   said interface and control computer of each said measuring module is distinct from said interface and control computer of each remaining said measuring module, and
   wherein each said measuring module is electronically and mechanically joined to other said measuring modules positioned adjacent to the mutually orthogonal sides of said each measuring module.

2. The expandable platform for measuring plantar pressures of claim 1, wherein the mutually orthogonal sides together define a square shape.

3. The platform according to claim 1, further comprising snap fittings, wherein one of said mutually orthogonal sides of said each measuring module is connected to an adjacent one of said mutually orthogonal sides of each of said other measuring modules by said snap fittings.

4. The platform according to claim 1, further comprising snap fittings, wherein snap fitting connect said other measuring modules to the least two of the mutually orthogonal sides of said each measuring module.

5. An expandable platform for measuring plantar pressures, the platform comprising:
   at least six measuring modules (1), each said measuring module for measuring plural plantar pressures, said each measuring module including
   i) four mutually orthogonal sides,
   ii) four walls, each wall of said four walls extending along at least part of a respective one of said four mutually orthogonal sides,
   iii) an array of sensors that measure the plural plantar pressures, the array of sensors being located within the mutually orthogonal sides, and
   iv) an interface and a control computer, both the interface and control computer being located within the four walls of said each measuring module,
   wherein the interface of said each measuring module is electronically connected to the array of sensors within the mutually orthogonal sides, and is electronically connected to the control computer within the mutually orthogonal sides,
   wherein each control computer is provided with software for treatment of information transmitted from the array of sensors of each of the respective said measuring modules through the respective interface, and
   wherein a first of said measuring modules includes
   i) a first of the mutually orthogonal sides that is electronically and mechanically joined to a first of the mutually orthogonal sides of a second of said measuring modules, and
   ii) a second of the mutually orthogonal sides that is electronically and mechanically joined to a first of the mutually orthogonal sides of a third of said measuring modules, and
   iii) a third of the mutually orthogonal sides that is electronically and mechanically joined to a first of the mutually orthogonal sides of a fourth of said measuring modules,
   wherein a second of the mutually orthogonal sides of said second measuring module is electronically and mechanically joined to a first of the mutually orthogonal sides of a fifth of said measuring modules,
   wherein a second of the mutually orthogonal sides of said fifth measuring module includes is electronically and mechanically joined to a second of the mutually orthogonal sides of said third measuring module,
   wherein a third of the mutually orthogonal sides of said third measuring module includes is electronically and mechanically joined to a first of the mutually orthogonal sides of a sixth of said measuring modules, and
   wherein said fourth measuring module is electronically joined to said first measuring module, said first measuring module is electronically joined to said second measuring module, said second measuring module is electronically joined to said fourth measuring module, fourth measuring module is electronic joined to said third measuring module, and said third measuring module is electronically joined to said sixth measuring module,
   wherein said interface and control computer of each said measuring module is distinct from said interface and control computer of each remaining said measuring module.

6. The platform according to claim 5, further comprising snap fittings, wherein the snap fittings mechanically connects
   i) the first of the mutually orthogonal sides of said first measuring module to the first of the mutually orthogonal sides of said second measuring module,
   ii) the second of the mutually orthogonal sides of said first measuring module to the first of the mutually orthogonal sides of said third measuring module, and
   iii) the third of the mutually orthogonal sides of said first measuring module to the first of the mutually orthogonal sides of said fourth measuring module.

7. The platform according to claim 1, wherein said four walls of each said measuring module keeps each said measuring module raised above a ground surface.

8. The platform according to claim 1, wherein said four mutually orthogonal sides define corners of each said measuring module, and said four walls of each said measuring module do not extend to said corners.

9. The platform according to claim 5, wherein said four walls of each said measuring module keeps each said measuring module raised above a ground surface.

10. The platform according to claim 5, wherein said four mutually orthogonal sides define corners of each said measuring module, and said four walls of each said measuring module do not extend to said corners.

\* \* \* \* \*